(12) United States Patent
Lefebvre et al.

(10) Patent No.: US 10,337,986 B2
(45) Date of Patent: Jul. 2, 2019

(54) METHOD FOR OPTIMISATION OF DETECTION WAVELENGTHS FOR MULTI-GAS DETECTION

(71) Applicant: Commissariat A L'Energie Atomique et aux Energies Alternatives, Paris (FR)

(72) Inventors: Anthony Lefebvre, Seyssinet-Pariset (FR); Sebastien Becker, Voiron (FR); Salim Boutami, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 59 days.

(21) Appl. No.: 15/279,955

(22) Filed: Sep. 29, 2016

(65) Prior Publication Data
US 2017/0097301 A1 Apr. 6, 2017

(30) Foreign Application Priority Data

Oct. 1, 2015 (FR) ...................... 15 59328

(51) Int. Cl.
*G01N 21/27* (2006.01)
*G01N 21/31* (2006.01)
(Continued)

(52) U.S. Cl.
CPC ........... *G01N 21/274* (2013.01); *G01N 21/31* (2013.01); *G01N 21/3504* (2013.01);
(Continued)

(58) Field of Classification Search
CPC .. G01N 21/3504; G01N 21/61; G01N 21/274; G01N 21/39; G01N 2201/12746;
(Continued)

(56) References Cited

U.S. PATENT DOCUMENTS 4,914,719 A 4/1990 Conlon et al.
5,041,723 A 8/1991 Ishida et al.
(Continued)

FOREIGN PATENT DOCUMENTS

EP 0 544 962 A1 6/1993

OTHER PUBLICATIONS

U.S. Appl. No. 14/617,042, filed Feb. 9, 2015, US 2015/0226612 A1, Ujwol Palanchoke, et al.
(Continued)

*Primary Examiner* — Bryan Bui
(74) *Attorney, Agent, or Firm* — Oblon, McClelland, Maier & Neustadt, L.L.P.

(57) ABSTRACT

A method for optimizing values of n detection wavelengths of an optical gas sensor configured to detect n different gases is provided, including: a) calculating a value of a determinant of an absorptivity matrix ε whose coefficients represent spectral absorptivity of each of the n different gases at the n detection wavelengths, the calculating being repeated several times, each time modifying at least one of said n detection wavelengths so the values of said n detection wavelengths are comprised within a range of values for which the spectral absorptivity of at least one of the n different gases is non-zero; and b) determining the values of said n detection wavelengths for which the calculated value of the determinant of the absorptivity matrix ε corresponds to a maximum calculated value amongst a set of values calculated in step a).

12 Claims, 3 Drawing Sheets

(51) Int. Cl.
*G01N 21/61* (2006.01)
*G01N 21/3504* (2014.01)

(52) U.S. Cl.
CPC ..... *G01N 21/61* (2013.01); *G01N 2021/3133* (2013.01); *G01N 2021/3137* (2013.01); *G01N 2201/12746* (2013.01)

(58) Field of Classification Search
CPC ......... G01N 2201/12764; G01N 21/31; G01N 2021/3133; G01N 2021/3137
See application file for complete search history.

(56) References Cited

U.S. PATENT DOCUMENTS

| | | | |
|---|---|---|---|
| 5,281,817 | A | 1/1994 | Yelderman et al. |
| 5,306,913 | A | 4/1994 | Noack et al. |
| 6,307,201 | B1 | 10/2001 | Didomenico et al. |
| 9,547,137 | B2 | 1/2017 | Favreau et al. |
| 9,562,936 | B2 | 2/2017 | Becker et al. |
| 2003/0081204 | A1 | 5/2003 | Cronin et al. |
| 2010/0253933 | A1* | 10/2010 | Guieze ............... G01N 21/33 356/51 |
| 2015/0099274 | A1* | 4/2015 | Axelrod ............... C12M 41/34 435/39 |
| 2017/0322149 | A1* | 11/2017 | Pape ............... G01N 21/3504 |

OTHER PUBLICATIONS

U.S. Appl. No. 14/865,546, filed Sep. 25, 2015, US 2016/0091371 A1, Ujwol Palanchoke, et al.
French Search Report dated Jun. 15, 2016 in Patent Application No. FR 1559328 (with English translation of categories of cited documents).
C. B. Lucasius, et al., "Genetic Algorithms in Wavelength Selection: a Comparative Study", Analytica Chimica Acta, Elsevier, vol. 286, No. 2, Feb. 18, 1994, pp. 135-153.
Zou Xiaobo, et al., "Variables Selection Methods in Near-Infrared Spectroscopy", Analytica Chimica Acta, Elsevier, vol. 667, No. 1-2, May 14, 2010, pp. 14-32.
Nikolaus Hansen, "The CMA Evolution Strategy: A tutorial" ((https://www.iri.fr/hansen/cmatutorial 110628), 2005, pp. 1-34.
Chris W. Brown, et al., "Matrix Representations and Criteria for Selecting Analytical Wavelengths for Multicomponent Spectroscopic Analysis", Analytical Chemistry, No. 54, No. 9, Aug. 1982, pp. 1472-1479.
James Kennedy, et al., "Particle Swarm Optimization", Neural Networks, Proceedings, IEEE International Conference on, vol. 4, 1995, pp. 1942-1948.
Edward Naranjo, et al., "IR Gas Imaging in an Industrial Setting", Proceedings of SPIE—The International Society for Optical Engineering (Impact Factor: 0.2). vol. 7661, Apr. 2010, pp. 76610K-1-76610K-8.

\* cited by examiner

METHOD FOR OPTIMISATION OF DETECTION WAVELENGTHS FOR MULTI-GAS DETECTION

TECHNICAL FIELD AND PRIOR ART

The invention relates to the field of optical spectroscopy and more particularly that of the detection of chemical species in gas or liquid phase by spectral absorption.

Figure 1:
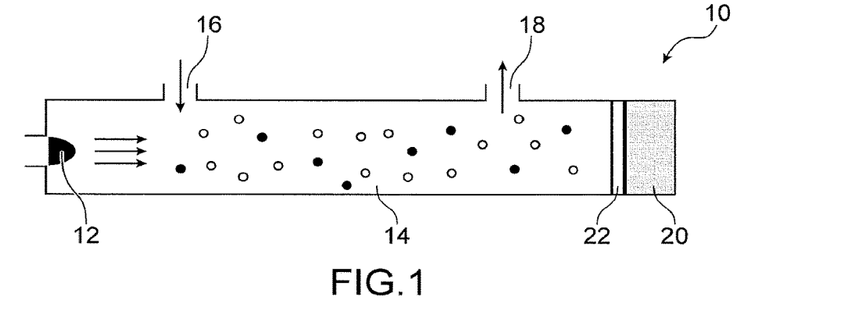
FIG. 1 shows an optical gas sensor of the NDIR type.

An optical gas sensor, more particularly a Non-Dispersive Infra-Red (NDIR) sensor, can be used to calculate the concentration of a gas in liquid or vapour phase. It comprises an infra-red source whose radiation is directed through a cell wherein the gas to be detected is located, towards a detector which is generally provided with a spectral filter. FIG. 1 shows a schematic representation of such a sensor 10 comprising an infra-red light source 12 arranged in a cell 14 possessing an inlet 16 and an outlet 18 through which the gas enters and leaves the cell 14. Infra-red light radiation emitted by the source 12 is directed towards a detector 20 and passes through a spectral filter 22 before reaching the detector 20. Alternatively, the source 12 may be a laser light source and in this case the sensor 10 does not comprise a spectral filter, due to the monochromatic character of the light emitted by such a source.

Since most gases each possess a distinct signature in the mid-infra-red range (for example wavelengths between about 3 µm and 15 µm), a proportion of the infra-red radiation emitted by the source 12 in the MIR range is absorbed by the gas present in the cell 14 and the reduction in the intensity of the light signal which results from this absorption is quantified by comparison with a reference path which is not subject to this variation. This phenomenon is described by the Beer-Lambert law, which states that:

$$T(\lambda) = \frac{I(\lambda)}{I_0(\lambda)} = 10^{-\varepsilon(\lambda)LC} \quad (1)$$

where $\lambda$ is the wavelength in question, $T(\lambda)$ the transmittance through the gas (that is without taking into account the filtering performed by the spectral filter 22), $I(\lambda)$ the outlet spectral intensity (measured by the detector), $I_0(\lambda)$ the inlet spectral intensity (emitted by the source), $\varepsilon(\lambda)$ the spectral absorption coefficient of the gas, L the length of the cavity crossed by the infra-red radiation and C is the concentration of the gas in the cavity.

In general the length L of the cavity is known, as is the spectral absorption coefficient $\varepsilon(\lambda)$ of the gas, which may be measured via prior calibration. The inlet spectral intensity $I_0(\lambda)$ is more difficult to measure and is often obtained from a reference path. This reference path generally consists of a second sensor provided with an optical filter located away from the absorption of the gas to be measured, for example arranged in a different cell to that into which the gas is introduced, and comprising a source which emits a light beam at a wavelength $\lambda_R$. This reference path is for example formed of elements similar to elements 12, 14, 20 and 22 of the sensor 10, the difference being for example that there is no gas present in this reference path. The transmittance $T(\lambda)$ of equation (1) is then obtained using the equation:

$$T(\lambda) = \left(\frac{I_{R0}(\lambda_R)}{I_{A0}(\lambda)}\right)\left(\frac{I_A(\lambda)}{I_R(\lambda_R)}\right) = 10^{-\varepsilon(\lambda)LC} \quad (2)$$

where $I_R(\lambda_r)=I_{R0}(\lambda_R)$ since the light beam does not undergo absorption by the gas in this reference path, and therefore $I_A(\lambda)=I_{A0}(\lambda)10^{-\varepsilon(\lambda)LC}$ given by equation (1). Here the index R indicates the reference path, the index A the active path and the index 0 a measurement at zero concentration (at the inlet to the cell). Calibration of the ratio $I_{R0}(\lambda_R)/I_{A0}(\lambda)$ and measurement of the ratio $I_A(\lambda)/I_R(\lambda_R)$ is used to calculate the transmittance $T(\lambda)$ through the gas. Using the logarithm of this transmittance $T(\lambda)$, it is possible to arrive at the concentration of the gas C:

$$C = -\frac{\log T(\lambda)}{\varepsilon(\lambda)L} \quad (3)$$

When the absorption by the gas is weak, it is possible to make equation (1) linear and the concentration C is then approximately proportional to the factor (1−T).

In the case where it is intended to measure and discriminate between two different gases, it is possible to use two independent active paths, each possessing a spectral filter positioned on the absorption spectrum of one of the first and second gases (or which each possess a laser light source emitting light beams at different wavelengths centred in relation to the gases' absorption spectra). Each path is then used to obtain information on the concentration of the gas for which it was designed.

This approach is, however, only valid when there is no overlap between the absorption spectra of the two gases, since otherwise there may be confusion between the two gases detected at a certain wavelength, and therefore a possible error in the result obtained. In order to resolve this uncertainty, it is necessary to cross the responses of the two sensors. The Beer-Lambert law according to equation (1) above is then expressed as follows for two gases:

$$\begin{cases} T(\lambda_1) = 10^{-(\varepsilon_1(\lambda_1)C_1+\varepsilon_2(\lambda_1)C_2)L} \\ T(\lambda_2) = 10^{-(\varepsilon_1(\lambda_2)C_1+\varepsilon_2(\lambda_2)C_2)L} \end{cases} \quad (4)$$

where $\lambda_1$ corresponds to the wavelength at which the first measurement is made (that is, the wavelength at which a first spectral filter of the sensor is placed whose bandwidth is of the order of the width of the absorption line for the first gas, or the wavelength emitted by a first laser light source of the sensor), and $\lambda_2$ corresponds to the wavelength at which the second measurement is made (that is the wavelength at which a second spectral filter of the sensor is placed whose bandwidth is of the order of the width of the absorption line of the second gas, or the wavelength emitted by a second laser light source of the sensor). From equations (4), two equations with two unknowns are deduced which may be solved in order to determine the concentrations $C_1$ and $C_2$ of the two gases:

$$\begin{cases} C_1 = -\frac{1}{L}\frac{\varepsilon_2(\lambda_2)\log T(\lambda_1) - \varepsilon_2(\lambda_1)\log T(\lambda_2)}{\varepsilon_1(\lambda_1)\varepsilon_2(\lambda_2) - \varepsilon_2(\lambda_1)\varepsilon_2 T(\lambda_1)} \\ C_2 = -\frac{1}{L}\frac{\varepsilon_1(\lambda_1)\log T(\lambda_2) - \varepsilon_1(\lambda_2)\log T(\lambda_1)}{\varepsilon_1(\lambda_1)\varepsilon_2(\lambda_2) - \varepsilon_1(\lambda_2)\varepsilon_2 T(\lambda_1)} \end{cases} \quad (5)$$

In the case where $\varepsilon_1(\lambda_2)=\varepsilon_2(\lambda_1)=0$ (no overlap between the absorption spectra of the two gases at wavelengths $\lambda_1$ and $\lambda_2$), the equations above become simplified to give two independent equations (3). In the converse case, there can be confusion between the detected gases.

The above case can apply to the detection of n gases, where n>2. A system of n equations with n unknowns, which may be solved using various techniques, is then obtained. As indicated in the document by C. W. Brown et al., "Matrix representations and criteria for selecting analytical wavelengths for multicomponent spectroscopic analysis", Anal. Chem. 1982, 54(9), pp. 1472-1479, such a system may take the form of a matrix, where equations (1) and (4) for n gases may then be written:

$$\log\begin{pmatrix} T(\lambda_1) \\ T(\lambda_2) \\ \vdots \\ T(\lambda_n) \end{pmatrix} = -\begin{pmatrix} \varepsilon_1(\lambda_1) & \varepsilon_2(\lambda_1) & \cdots & \varepsilon_n(\lambda_1) \\ \varepsilon_1(\lambda_2) & \varepsilon_2(\lambda_2) & \cdots & \varepsilon_n(\lambda_2) \\ \vdots & \vdots & \ddots & \vdots \\ \varepsilon_1(\lambda_n) & \varepsilon_2(\lambda_n) & \cdots & \varepsilon_n(\lambda_n) \end{pmatrix}\begin{pmatrix} LC_1 \\ LC_2 \\ \vdots \\ LC_n \end{pmatrix} \quad (6)$$

This equation (6) can be written in a more condensed manner:

$$\log(T) = -(\varepsilon)(LC) \quad (7)$$

In equation (7) above, T and LC correspond to vectors and $\varepsilon$ corresponds to a matrix known as an absorptivity matrix. From equation (7), it can be seen that obtaining the vector LC involves a simple matrix inversion, thus finally giving:

$$(LC) = -(\varepsilon^{-1})\log(T) \quad (8)$$

In theory, it is sufficient for the matrix $\varepsilon$ to be reversible in order to guarantee the uniqueness of the LC solution vector. In other words, it is possible to pass from equation (7) to equation (8) if the values of the columns in the matrix $\varepsilon$ are independent, that is, if no linear combination exists for passing from spectral absorption coefficient values of one column (relating to one of the gases) to spectral absorption coefficient values of other columns (relating to other gases) of the matrix $\varepsilon$. The positioning of the measurements made in order to obtain the values of the vector T, that is, the $\lambda_i$ values, has a strong influence on the precision of the result obtained. In effect, an error due to measurement noise is propagated to the result which corresponds to the concentration value displayed. Thus by considering the case of two measurements made for two gases at wavelengths $\lambda_1$ and $\lambda_2$, the greater the ratios $\varepsilon_1(\lambda_1)/\varepsilon_2(\lambda_1)$ and $\varepsilon_2(\lambda_2)/\varepsilon_1(\lambda_2)$, the more reliable the measurement.

In documents U.S. Pat. Nos. 5,041,723, 4,914,719, 5,281,817 and U.S. Pat. No. 6,307,201, various methods are proposed for choosing the values of the wavelengths $\lambda_i$ at which the sensor filters are positioned or which correspond to the wavelengths emitted by the laser light source of the sensor. These approaches are, however, relatively empirical and cannot be generalised to any number and type of gas to be detected.

DESCRIPTION OF THE INVENTION

Thus there is a need to propose a method allowing optimum values of detection wavelengths to be determined, that is, wavelengths at which it is envisaged placing spectral filters or envisaged wavelengths of light beams to be emitted by the sensor's laser light sources), in order to reduce as much as possible the impact of measurement noise on the result obtained, irrespective of the number n of gases to be detected and irrespective of their absorption spectra, whether these spectra overlap or not.

In order to do this, one embodiment proposes a method for optimising the values of n detection wavelengths of an optical gas sensor suitable for carrying out detection of n different gases, comprising the implementation of the following steps:

a) calculation of a value of a determinant of an absorptivity matrix $\varepsilon$ whose coefficients represent the spectral absorptivity of each of the n gases at n detection wavelengths, step a) being repeated several times, each time modifying at least one of said n detection wavelengths and such that the values of said n detection wavelengths are within a range of values for which the spectral absorptivity of at least one of the n gases is non-zero;

b) determination of the values of said n detection wavelengths for which the value of the determinant of the absorptivity matrix $\varepsilon$ corresponds to the maximum value of the set of values calculated in step a).

Thus it is proposed a method by which, using an error calculation which judiciously uses the absorptivity matrix $\varepsilon$, the optimum detection wavelengths can be chosen at which the measurements are intended to be made by the sensor in order to discriminate the presence of different gases during an absorption spectroscopic measurement.

Unlike the methods of the prior art which are based on essentially empirical methods, this method can be applied to any number of gases and to any type of gas. Furthermore, this method applies both to an NDIR or multi-spectral type optical gas detector.

In a first configuration, the method may be such that:
the optical gas detector comprises at least n laser light sources,
the coefficients of the absorptivity matrix $\varepsilon$ correspond or are uniformly proportional to the spectral absorption coefficients of each of the n gases at the n detection wavelengths, and
the values of the n detection wavelengths determined in step b) correspond to the wavelengths of light beams capable of being emitted by the n laser light sources.

In a second configuration, the method may be such that:
the optical gas sensor comprises at least one polychromatic light source and at least n spectral filters each capable of being used for detection of one of the n gases.
the coefficients of the absorptivity matrix $\varepsilon$ correspond or are uniformly proportional to the mean spectral absorption coefficients of each of the n gases, weighted or not by the spectral responses of the n spectral filters, and
the values of the n detection wavelengths determined in step b) correspond to the wavelengths at which the spectral responses of the n spectral filters are located.

In this case, the coefficients, $\tilde{\varepsilon}_j(\lambda_i)$, of the absorptivity matrix $\varepsilon$ are such that:

$$\tilde{\varepsilon}_j(\lambda_i) = \frac{\int \varepsilon_j(\lambda) A_i(\lambda) S(\lambda) d\lambda}{\int A_i(\lambda) S(\lambda) d\lambda}$$

or such that:

$$\tilde{\varepsilon}_j(\lambda_i) = \int \varepsilon_j(\lambda) A_i(\lambda) S(\lambda) d\lambda$$

where $\lambda_i$ corresponds to the n detection wavelengths, with i being such that $1 \leq i \leq n$;

$\varepsilon_j(\lambda)$ corresponds to the spectral absorption coefficients for the n gases, with j being such that $1 \leq j \leq n$;

$A_i(\lambda)$ corresponds to the spectral responses of the n spectral filters;

S(λ) corresponds to the emission spectrum of the light source.

In this case the method may be such that:
the n spectral filters are chosen from amongst a set of m spectral filters, where m>n, for which an outline profile, a wavelength value at which the spectral response is positioned and a width of the spectral response of each of the spectral filters of said set of filters are predetermined, and the values of the n detection wavelengths are chosen from the values of wavelengths at which the spectral responses of the spectral filters of the said set of filters are positioned.

Thus this method may be applied to select, from several predefined filters, those which are most capable of reducing the errors depending on the number and nature of gases to be detected.

Alternatively, the method may be such that:
the n spectral filters have the same outline profile A(λ), and
the coefficients, $\tilde{\varepsilon}_j(\lambda_i)$, of the absorptivity matrix ε are such that:

$$\tilde{\varepsilon}_j(\lambda_i) = \frac{\int A_i(\lambda)\varepsilon_j(\lambda)S(\lambda)d\lambda}{\int A_i(\lambda)S(\lambda)d\lambda}$$

or such that:

$$\tilde{\varepsilon}_j(\lambda_i) = \int A_i(\lambda)\varepsilon_j(\lambda)S(\lambda)d\lambda$$

where $\lambda_i$ corresponds to the n detection wavelengths, with i being such that $1 \le i \le n$;

$\varepsilon_j(\lambda)$ corresponds to the spectral absorption coefficients for the n gases, with j being such that $1 \le j \le n$;

where $A_i(\lambda)$ corresponds to the spectral responses of the n filters positioned at the wavelengths $\lambda_i$;

S(λ) is the emission spectrum of the light source.

In this alternative the method is used to select, by using for the detection of each of the n gases a spectral filter of a given outline profile and of a given spectral response width, the positions of the most suitable filters, that is, the wavelengths at which the spectral responses of the spectral filters are positioned, in order to reduce errors depending on the number and nature of the gases to be detected.

In this case the method may be such that:
the spectral response widths of the n spectral filters are adjustable,
the iteration of step a) is repeated several times, each time by modifying the width of the spectral responses of the n spectral filters, and
step b) determines the values of the n detection wavelengths for which the value of the determinant of the absorptivity matrix ε corresponds to the maximum value of the set of values calculated during the multiple iterations of step a).

Thus the method also allows the spectral response width of the n spectral filters used to be optimised to reduce the errors as a function of the number and of the nature of the gases to be detected.

The method may be such that:
the optical gas sensor does not comprise a reference path and comprises n+1 measurement paths;
the coefficients of the absorptivity matrix ε correspond, or are uniformly proportional to the spectral absorption coefficients, mean or not, of each of the n gases, weighted or not by the spectral responses of the n spectral filters, from which are subtracted the spectral absorption coefficients of one of the n+1 measurement paths of the optical gas sensor serving as a reference path.

Thus when the optical gas sensor comprises no reference paths allowing a spectral absorption measurement to be made without gas being present in this path, the method can even so be implemented by using one of the measurement paths which the serves as a reference path. The path acting as a reference path may correspond to any whatsoever of the sensor's measurement paths. This amounts to optimally choosing n+1 detection wavelengths so as to maximise the determinant of the absorptivity matrix ε.

The steps a) and b) may be implemented for example using an optimisation method of the evolutionary algorithm equation solver type.

BRIEF DESCRIPTION OF THE ILLUSTRATIONS

The present invention will be better understood on reading the description of example embodiments given, purely as an indication and in no sense restrictively, making reference to the appended illustrations in which.

Identical, similar or equivalent parts of the various figures described hereafter have the same numerical references, to make it easier to move from one figure to another.

In order to make the figures more readable, the various parts shown in the figures are not necessarily shown at a uniform scale.

The various possibilities (variants and embodiments) must be understood as not being mutually exclusive, and being capable of being combined with one another.

DETAILED DESCRIPTION OF SPECIFIC EMBODIMENTS

During a measurement of gas concentrations by the optical gas sensor 10 as described above, the main sources of error come from the source of radiation 12 and the detector 20 used. Assuming that the source 12 emits a spectral intensity $I \pm \sigma_{I_{source}}$, where $\sigma_{I_{source}}$ corresponds to the source noise 12, and that the detector 20 adds a noise $\sigma_{I_{capteur}}$, then a signal $I \pm \sigma$, where $\sigma_I^2 = \sigma_{I_{source}}^2 + \sigma_{I_{capteur}}^2$ is the end result. Depending on the case, the noise term coming from the source 12 or from the detector 20 predominates, but it is difficult to disassociate them. In practice it is easier to measure $\sigma_I$ directly as the standard deviation of the signal measured by the sensor 10 under set conditions. In calculating the transmittance $T=I/I_0$, noise $\sigma_T$ can be defined as:

$$\left(\frac{\sigma_T}{T}\right)^2 = \left(\frac{\sigma_I}{I}\right)^2 + \left(\frac{\sigma_{I_0}}{I_0}\right)^2 \quad (9)$$

In the case of a sensor 10 capable of carrying out the detection of n gases, n transmittances $T_i$ are measured, each with a given uncertainty $\sigma_{Ti}(i \in [1 \ldots n])$. These values are found on the diagonal of the associated covariance matrix $\Sigma_T$, with the values outside the diagonals being null values:

$$(\Sigma_T) = \begin{pmatrix} \sigma_{T1}^2 & 0 & \ldots & 0 \\ 0 & \sigma_{T2}^2 & \ldots & 0 \\ \vdots & \vdots & \ddots & \vdots \\ 0 & 0 & \ldots & \sigma_{Tn}^2 \end{pmatrix} \quad (10)$$

The error in the transmittances creates an error in the LC products propagating through equation (8) and leads to the following formula for the LC covariance matrix:

$$(\Sigma_{LC}) = (\varepsilon^{-1})(J_f)(\Sigma_T)(J_f)^t(\varepsilon^{-1})^T \quad (11)$$

Where $J_f$ is the Jacobean matrix of the function f: $\mathbb{R}^n \to \mathbb{R}^n$ defined by:

$$f(T_1, \ldots T_n) = \begin{cases} f_1(T_1, \ldots T_n) \\ \vdots \\ f_n(T_1, \ldots T_n) \end{cases} = \begin{cases} -\log T_1 \\ \vdots \\ -\log T_n \end{cases} \quad (12)$$

The Jacobean matrix $J_f$ of this function f may therefore be written in accordance with the equation:

$$J_F = -\frac{1}{\ln 10}\begin{pmatrix} 1/T_1 & 0 & \ldots & 0 \\ 0 & 1/T_1 & \ldots & 0 \\ \vdots & \vdots & \ddots & \vdots \\ 0 & 0 & \ldots & 1/T_n \end{pmatrix} \quad (13)$$

Furthermore, in the above equation (11), the inverse of the matrix ε may be expressed as a function of its determinant and of its comatrix by the equation:

$$\varepsilon^{-1} = \frac{1}{det(\varepsilon)} {}^tcom(\varepsilon) \quad (14)$$

The general formulae above are valid irrespective of the number of gases n to be detected and may be supplemented if other sources of errors exist. More specifically, it is possible to write the extended version of variances of the equation (11) in the case of a sensor that is capable of carrying out detection of two gases:

$$\begin{cases} \sigma_{LC_1}^2 = \left(\frac{1}{\ln 10(\varepsilon_{11}\varepsilon_{22} - \varepsilon_{21}\varepsilon_{12})}\right)^2\left[\left(\frac{\varepsilon_{22}\sigma_{T1}}{T_1}\right)^2 + \left(\frac{\varepsilon_{12}\sigma_{T2}}{T_2}\right)^2\right] \\ \sigma_{LC_2}^2 = \left(\frac{1}{\ln 10(\varepsilon_{11}\varepsilon_{22} - \varepsilon_{21}\varepsilon_{12})}\right)^2\left[\left(\frac{\varepsilon_{21}\sigma_{T1}}{T_1}\right)^2 + \left(\frac{\varepsilon_{11}\sigma_{T2}}{T_2}\right)^2\right] \end{cases} \quad (15)$$

By using the expressions of equation (11) it is possible to evaluate the error precisely over all concentrations to be measured as a function of the values of the matrix ε which correspond to the various gas absorption lines and the concentrations of various gases. It is therefore possible to select n wavelengths around which the n filters must be positioned (from the corresponding ε matrix) so as to comply with a well-defined specification: all errors below a certain threshold value, a different precision for each gas etc. Due to the fact that a filter corresponds to an outline profile which may be translated over a range of wavelengths, the positioning of the filters corresponds to the positioning of its outline profile relative to a reference wavelength. This reference wavelength may change according to the shape of the filter outline profile. For example, the positioning of a Gaussian filter, or any other filter whose outline profile is symmetric in relation to a central wavelength, can be carried out by choosing the central wavelength of the spectral response of the filter as the reference wavelength. For a high-pass or low-pass type filter, the reference wavelength may correspond, for example, to the filter cut-off wavelength.

In general, however, it is difficult to optimise the system with the n diagonal values of the matrix ($\Sigma_{LC}$). For example, in the variances expressed in equation (15), these comprise two distinct terms: the first is proportional to the inverse of the squared determinant (which corresponds to the terms $$\left(\frac{1}{\ln 10(\varepsilon_{11}\varepsilon_{22} - \varepsilon_{21}\varepsilon_{12})}\right)^2 \text{ for } \sigma_{LC_1}^2 \text{ and } \sigma_{LC_2}^2\right),$$

and the second takes into account the errors in the absence of gas on the transmittance and contains co-factors of the squared matrix ε (which corresponds to the terms $$\left[\left(\frac{\varepsilon_{22}\sigma_{T1}}{T_1}\right)^2 + \left(\frac{\varepsilon_{12}\sigma_{T2}}{T_2}\right)^2\right] \text{ for } \sigma_{LC_1}^2 \text{ and}$$

$$\left[\left(\frac{\varepsilon_{21}\sigma_{T1}}{T_1}\right)^2 + \left(\frac{\varepsilon_{11}\sigma_{T2}}{T_2}\right)^2\right] \text{ for } \sigma_{LC_2}^2\right).$$

To diminish the set of errors it is proposed to maximise the determinant in the first terms stated above. The determinant of the absorptivity matrix ε is therefore used as a performance indicator for the selection of wavelengths to be used for the detection of the gases. The greater the latter's absolute value, then the smaller is the overall error in the determination of concentrations.

In general, the method for optimising the values of n detection wavelengths of an optical gas sensor capable of carrying out detection of n different gases comprises the implementation of the following steps:

a) calculation of a value of the determinant of the absorptivity matrix ε whose coefficients represent the spectral absorptivity of each of the n gases at n detection wavelengths, step a) being repeated several times, each time modifying at least one of said n detection wavelengths and such that the values of said n detection wavelengths are comprised within a range of values for which the spectral absorptivity of at least one of the n gases is non-zero;

b) determination of the values of said n detection wavelengths for which the value of the determinant of the absorptivity matrix ε corresponds to the maximum value amongst the set of values calculated in step a).

All potential detection wavelengths are therefore evaluated by seeking to maximise this determinant. For a small number n of gases, for example for n≤4, it is possible to turn to an exhaustive method and test all the possible detection wavelengths. For a large number n of gases, for example for n≥5, an optimisation method of the equation solver type can be used, corresponding for example to evolutionary algorithms such as the "Particle Swarm Optimisation" or PSO algorithm described in the document "Particle Swarm Optimization" by J. Kennedy et al., Neural Networks, 1995. Proceedings., IEEE International Conference on, vol. 4, pp. 1942-1948, or the "Covariance Matrix Adaptation Evolution Strategy" or CMAES algorithm of N. Hansen, "The CMA evolution strategy: A tutorial".

If necessary, once the maximum value determinant has been found, it is possible to calculate exact values of the errors in transmittances from equation (11) in order to verify that the determined values do not cause saturation problems.

The method described above gives good results for a set of discrete $\lambda_i$ values, and is suitable when the sensor comprises laser light sources which are monochromatic. In this case the method allows the optimum wavelengths $\lambda_i$ emitted by the n laser light sources of the sensor to be identified.

When a polychromatic light source is used with filters whose spectral widths are greater than those of the absorption lines of the gases to be detected, instead of directly using the values of the spectral absorption coefficients $\varepsilon(\lambda)$ of the gases in the absorptivity matrix ε, the coefficients of the absorptivity matrix ε are chosen as corresponding to the mean spectral absorption coefficients of each of the n gases, weighted by the spectral responses of the n special filters. These coefficients are calculated according to the following equation:

$$\tilde{\varepsilon}_j(\lambda_i) = \frac{\int \varepsilon_j(\lambda) A_i(\lambda) S(\lambda) d\lambda}{\int A_i(\lambda) S(\lambda) d\lambda} \quad (16)$$

where $\tilde{\varepsilon}_j(\lambda_i)$ is the mean spectral absorption coefficient of the gas j in relation to a spectral filter whose typical spectral response $A_i$ is located at the wavelength $\lambda_i$, and $S(\lambda)$ is the emission spectrum of the light source. The indexes i and j are such that $1 \le i \le n$ and $1 \le j \le n$. The term $\varepsilon_j(\lambda)$ corresponds to the spectral absorption coefficient of the gas j. The calculation of the coefficients $\tilde{\varepsilon}_j(\lambda_i)$ is carried out by integrating formula (16) above over the entire domain in which $\varepsilon_j(\lambda)$ and $A_i(\lambda)$ are substantially non-zero. This generally means performing this integration over the domain which corresponds to the width of the filter until $A_i(\lambda)$ is more or less zero.

The application of equation (16) above corresponds to the application of a filter of a given typical outline profile (A), this filter being repeated for different values of $\lambda_i$ in order to simulate several filter positionings. In one particular embodiment, when the filters to be used in the sensor are chosen from amongst a given set of filter whose transfer functions, or spectral responses, are defined (outline profile, width and central wavelength defined), it is possible to calculate the corresponding values $\tilde{\varepsilon}_{ij}$ and to obtain the sub-set of filters which maximise the value of the determinant of the absorptivity matrix ε. The most highly optimised filters amongst those available are thus identified for use in the sensor.

When the positions of the spectral filters, that is, the wavelengths at which the spectral responses of the filters are located, are not defined and can be chosen, but where the spectral filters have a defined width and outline profile (that is, it is possible to position, in terms of the spectrum, a spectral filter of form A at any wavelength $\lambda_i$ whatsoever, as in the case of interference filters whose filter parameters are modified by modifying the parameters of the layers used for making them), then it is possible to construct the function $\tilde{\varepsilon}_j(\lambda_i)$ using equation (16) above to scan all possible values of the positioning $\lambda_i$ in the range that is of interest.

In the case where, in addition to the free positioning of the spectral filters, the spectral response widths of the filters are variable, the operation described above can be repeated for each possible width of the spectral response of the filters, and optimum filters chosen by varying these two parameters for the creation of the matrix ε. In this case it is possible to reduce the error even further by making the filter widths correspond to the absorption line widths (for example by using the absorption line half-height widths).

However, the possibility of having different filter widths will make the search converge on very narrow filters whose mean emissivity is greater. In the case where the spectral power outputted by the light source is limited (in the case of a black body-like source for example), this also means reducing the spectral intensity of the signal and increasing the error if the noise is constant.

When the positions of the filters are predefined and cannot be modified, the coefficients of the absorptivity matrix ε can be calculated using the following equation:

$$\tilde{\varepsilon}_j(\lambda_i) = \int \varepsilon_j(\lambda) A_i(\lambda) S(\lambda) d\lambda \quad (17)$$

It is thus possible to easily allow for the quantity of luminous flux which reaches the detector, and which is proportional to the term $\int A_i(\lambda) S(\lambda) d\lambda$, and to find an optimum which takes the quantity of the luminous flux which reaches the detector into account, irrespective of the filter spectral width.

In the cases described above, the use of mean absorptivities to form the coefficients of the absorptivity matrix ε is preferable in the case of low gas concentrations for which the exponential regime of the Beer-Lambert law is linear. The mean transmittance is not in fact the mean of the transmittances, that is:

$$[10^{-\varepsilon_j(\lambda)LC_i}]_\lambda \ne 10^{-[\varepsilon_j(\lambda)]_\lambda LC_i}, \quad (18)$$

Advantageously, it is preferable not to have a parameter $\varepsilon(\lambda).LC$, which relates to the transmittance of the gas alone, which is greater than about 4% in order to guarantee that the difference between the exponential and its linearization remains at about 5%.

An example is described below in order to illustrate the methods described above.

Figure 2:
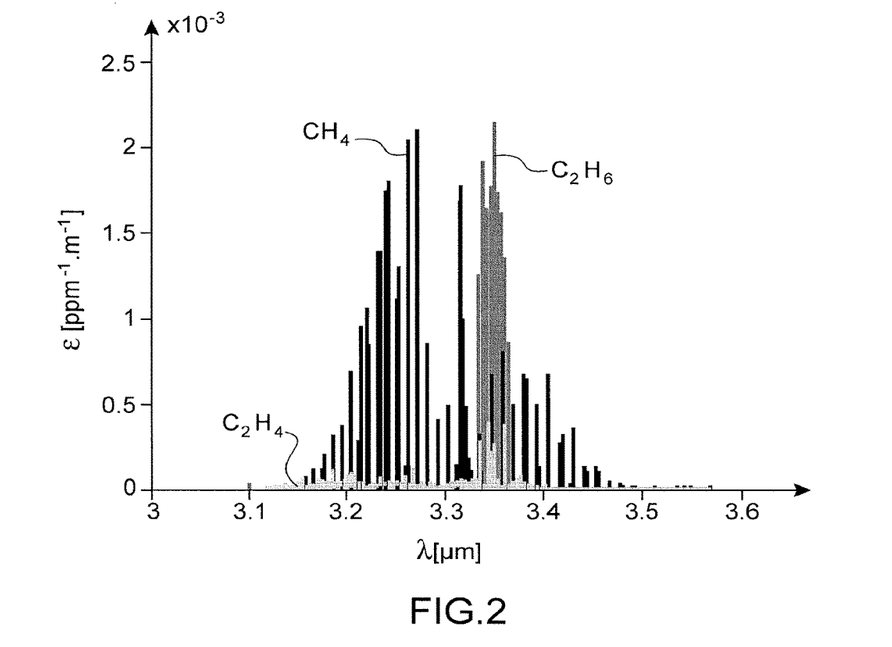
FIG. 2 shows absorption spectra, or spectral absorption coefficients, for three gases intended to be detected by a sensor optimised by the implementation of a method for optimisation of the detection wavelength values of the detector according to one particular embodiment.

This example is implemented in order to determine the characteristics of three filters of an NDIR detector capable of discriminating three gases, here three hydrocarbons: methane $CH_4$, ethane $C_2H_6$ and ethylene $C_2H_4$. The absorption spectra, that is, the spectral absorption coefficients of the three gases are shown in FIG. 2. This figure shows that the absorption spectra overlap significantly and that the choice of characteristics of the filters, in particular the detection wavelengths at which it is intended to locate the spectral responses of the filters, is not obvious.

Figure 3:
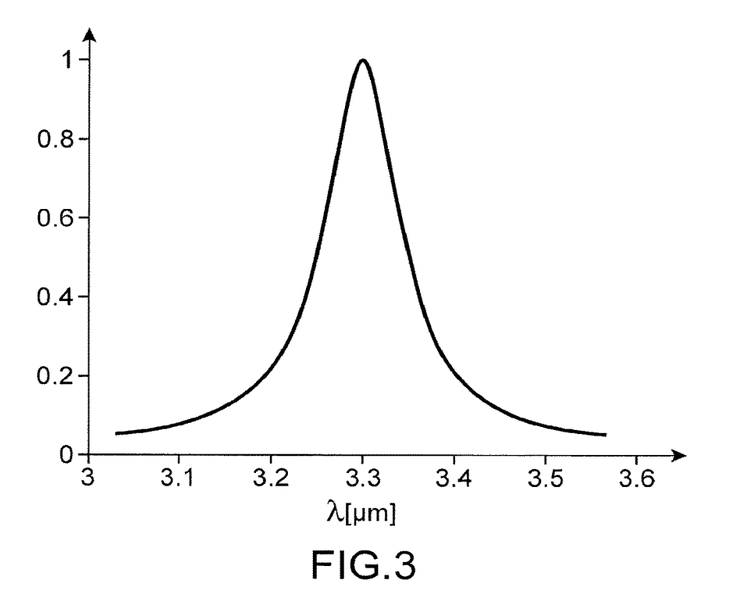
FIG. 3 shows a sensor filter outline profile optimised by the implementation of the method of optimisation of detection wavelength values according to the particular embodiment.

A Lorentzian filter, whose outline profile is shown in FIG. 3, is for example chosen in this implementation example. This outline profile, centred on $\lambda_i$ and of width $\Gamma$ is expressed in accordance with the equation:

$$A_i(\lambda) = \frac{1}{1+\left(\frac{\lambda-\lambda_i}{\Gamma/2}\right)^2} \tag{19}$$

Other types of filters may be used, for example a Gaussian filter.

Figure 4:
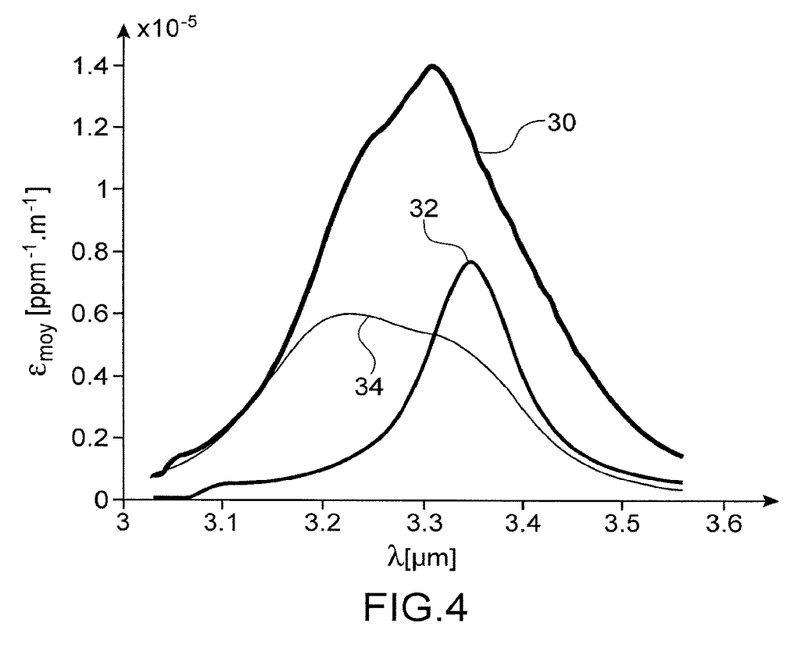
FIG. 4 shows the convolution products of the filter outline profile shown in FIG. 3 with the absorption spectra shown in FIG. 2.

The coefficients of the absorptivity matrix E are calculated in accordance with equation (16) above. The terms $\tilde{\varepsilon}_j(\lambda_i) = \int A_i(\lambda)\varepsilon_j(\lambda)S(\lambda)d\lambda$ of this equation correspond to the convolution products of the filter response with the absorption spectrum of each of the three gases and are shown in FIG. 4. Reference 30 designates the convolution product of the absorption spectrum of methane with the filter outline profile shown in FIG. 3, reference 32 designates the convolution product of the absorption spectrum of ethane with the filter outline profile shown in FIG. 3, and reference 34 designates the convolution product of the absorption spectrum of ethylene with the filter outline profile shown in FIG. 3. The effect of such a convolution is to smooth the gas absorption spectra, which allows a coarser spectral discretisation to be chosen, thus reducing the calculation time required to calculate the maximum value determinant of the absorptivity matrix ε.

Figure 5:
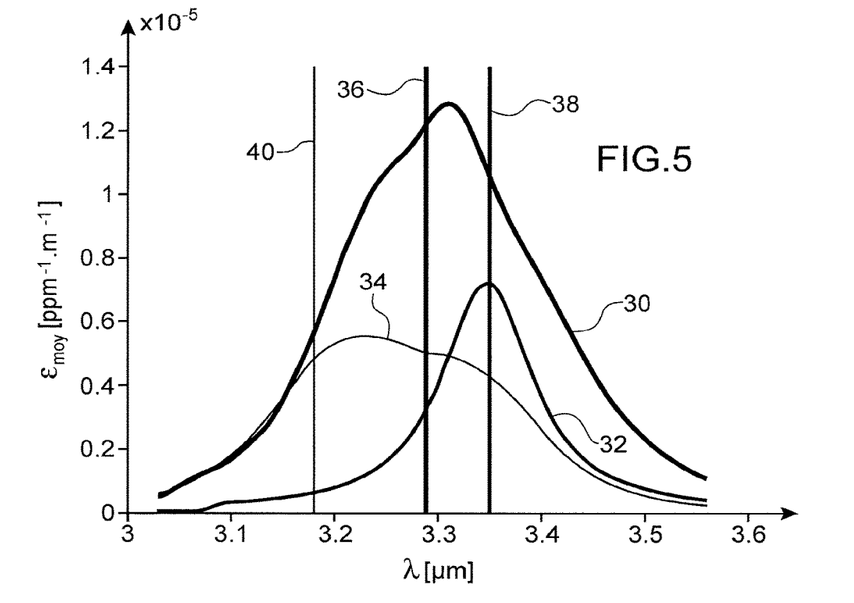
FIG. 5 shows the detection wavelengths calculated during the implementation of the method according to the particular embodiment and superimposed on the convolution products of FIG. 4.
Figure 6:
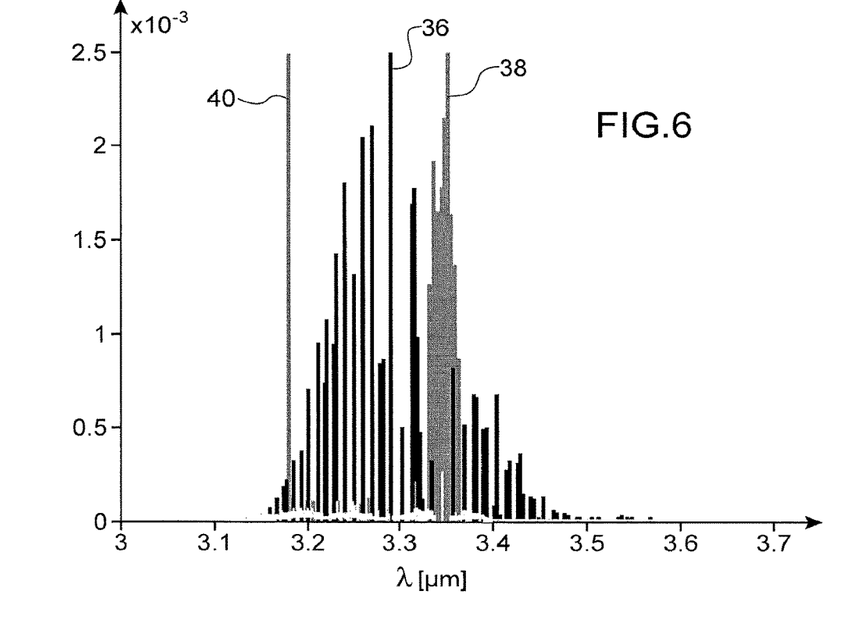
FIG. 6 shows the detection wavelengths calculated during the implementation of the method according to the particular embodiment and superimposed on the absorption spectra of FIG. 2.

The determinant of the absorptivity matrix ε whose coefficients correspond to the mean absorptivities $\tilde{\varepsilon}_j(\lambda_i)$ is calculated for several possible positions of the filters. The optimum positions of the filters, which correspond to the positions for which the value of this determinant is maximised, are calculated and shown in FIG. 5 wherein these positions are superimposed on the mean absorption spectra, and in FIG. 6 wherein these positions are superimposed on the initial absorption spectra of the gases. Thus a first detection wavelength 36 at which the spectral response of a first of three filters intended to detect methane is calculated and is here equal to about 3.29 μm, a second detection wavelength 38 at which the spectral response of a second of three filters intended to detect ethane is calculated and is here equal to about 3.35 μm, and a third detection wavelength 40 at which the spectral response of a third of three filters intended to detect ethylene is calculated and is here equal to about 3.18 μm. These FIGS. 5 and 6 show clearly that the optimum positions for the filters, that is the detection wavelengths at which the spectral responses of the filters are found do not always correspond to the maximum values of the absorption spectra of the gases to be detected.

After the calculation of these detection wavelengths, it is possible to calculate the errors in the concentrations by using equation (11) above from transmission errors and measured concentrations.

In certain cases it is impossible to use filters which have good rejection, that is, which effectively cut off the wavelengths outside the selected spectral band. In the case where a wide band absorption background persists, it is impossible to create a reference path which is not sensitive to the presence of gases. The case wherein the sensor does not comprise a reference path or in which one of the measurement paths is used as a reference path is described below.

In such a configuration, by considering two measurement paths, the transmittance is then defined by the following equation:

$$T = \left(\frac{I_{20}}{I_{10}}\right)\left(\frac{I_1}{I_2}\right) = \frac{10^{-\varepsilon_1(\lambda_1)LC}}{10^{-\varepsilon_1(\lambda_r)LC}} = 10^{-[(\varepsilon_1(\lambda_1)-\varepsilon_1(\lambda_r))LC]} \tag{20}$$

Here the second path is regarded as being the reference path, and $\varepsilon_1(\lambda_r)$ is the absorptivity of the first gas seen by the filter associated with this reference path. The equation (20) is very similar to the equation (2), the difference being that the term $\varepsilon_1(\lambda_1)$ is replaced by the term $(\varepsilon_1(\lambda_1)-\varepsilon_1(\lambda_r))$. The steps in the methods described above may therefore be applied by considering, instead of absorptivities of each of the paths, the differences between these absorptivities and that of the path acting as a reference.

When n gases are considered, n measurement filters and one reference filter, with a reference of r, are used. The absorptivity matrix ε described above in equation (6) is in this case replaced by the following matrix:

$$\begin{pmatrix} (\varepsilon_1(\lambda_1)-\varepsilon_1(\lambda_r)) & (\varepsilon_2(\lambda_1)-\varepsilon_2(\lambda_r)) & \cdots & (\varepsilon_n(\lambda_1)-\varepsilon_n(\lambda_r)) \\ (\varepsilon_1(\lambda_2)-\varepsilon_1(\lambda_r)) & (\varepsilon_2(\lambda_2)-\varepsilon_2(\lambda_r)) & \cdots & (\varepsilon_n(\lambda_2)-\varepsilon_n(\lambda_r)) \\ \vdots & \vdots & \ddots & \vdots \\ (\varepsilon_1(\lambda_n)-\varepsilon_1(\lambda_r)) & (\varepsilon_2(\lambda_n)-\varepsilon_2(\lambda_r)) & \cdots & (\varepsilon_n(\lambda_n)-\varepsilon_n(\lambda_r)) \end{pmatrix} \tag{21}$$

In the above matrix (21), the row vector of the absorptivity of the path acting as a reference is subtracted at every row in the initial absorptivity matrix used in the equation (6) above. In the calculation method, this amounts to placing n+1 filters in an optimum manner in order to maximise the determinant of the matrix (21).

It should be noted that the best results are obtained when it is possible to have a path independent of all the gases, which corresponds to a conventional reference path. Finally, when one of the sensor paths is used as a reference path, the choice of one specific filter rather than another for this reference path has no effect on the result obtained.

In the examples described above, the sensor used corresponds to a sensor which comprises a cavity of known length L, such as the NDIR sensor 10. Nevertheless, these methods can also be applied to a multi-spectral imager wherein a sensor is for example coupled to a filter wheel as described in the document "IR Gas Imaging in an Industrial Setting" by E. Naranjo et al., Proceedings of SPIE—The International Society for Optical Engineering (Impact Factor: 0.2). April 2010, vol. 7661, pp. 76610K-76610K-8, which can be used to select, via a choice of filters, either an active path influenced by the presence of gas, or a reference path. The filter wheel can be replaced by selective absorbers formed at the pixel level (MIM resonators, pixellic filters etc.).

In such an imagery system, the optical system is passive, and radiation similar to that of a black body located in the background is used as a light source. The signal measured by a pixel filtered by a path i is proportional to a received flux $\phi_i$, which is expressed by the following equation:

$$\phi_i = \int [\phi_{BB}(T_B)T(\lambda)+\phi_{BB}(T_C)(1-T(\lambda))]A_i(\lambda)d\lambda \tag{22}$$

where $\phi_{BB}$ is the luminance of the black body given by the Planck equation, $T_B$ and $T_C$ are respectively the background and gas temperatures, and $A_i(\lambda)$ the spectral response of the filter i.

By considering the flux difference between two adjacent pixels which are imaging two zones of different temperatures $T_{B1}$ and $T_{B2}$, a signal $\Delta\phi_i$ which is independent of the gas temperature is obtained:

$$\Delta\phi_i = \int [\phi_{BB}(T_{B2}) - \phi_{BB}(T_{B1})] T(\lambda) A_i(\lambda) d\lambda \quad (23)$$

From the ratio of the signal measured in an active path i and a reference path j, such that $T(\lambda)A_j(\lambda) = A_j(\lambda)$ (the gas does not absorb in the reference path), the following expression, similar to equation (2), is obtained:

$$\eta_{ij} = \frac{\int [\phi_{BB}(T_{B2}) - \phi_{BB}(T_{B1})] T(\lambda) A_i(\lambda) d\lambda}{\int [\phi_{BB}(T_{B2}) - \phi_{BB}(T_{B1})] A_j(\lambda) d\lambda} \approx \frac{\tilde{A}_i}{\tilde{A}_j} T \quad (24)$$

The terms $\tilde{A}$ correspond to spectral responses averaged at $\lambda$. By calibrating the ratio $\tilde{A}_i/\tilde{A}_j$, it is therefore possible to relate back to the length-concentration product using equation (3).

The invention claimed is:

1. A method for optimising values of n detection wavelengths of an optical gas sensor configured to detect n different gases, the method comprising:
   a) calculating a value of a determinant of an absorptivity matrix ε whose coefficients represent spectral absorptivity of each of the n different gases at the n detection wavelengths, said calculating being repeated several times, each time modifying at least one of said n detection wavelengths so the values of said n detection wavelengths are comprised within a range of values for which the spectral absorptivity of at least one of then different gases is non-zero; and
   b) determining the values of said n detection wavelengths for which the calculated value of the determinant of the absorptivity matrix ε corresponds to a maximum calculated value amongst a set of values calculated in step a).

2. The method according to claim 1, wherein:
   the optical gas sensor comprises at least n laser light sources,
   the coefficients of the absorptivity matrix ε correspond or are uniformly proportional to spectral absorption coefficients of each of then different gases at then detection wavelengths, and
   the values of the n detection wavelengths determined in step b) correspond to wavelengths of light beams configured to be emitted by the n laser light sources.

3. The method according to claim 1, wherein:
   the optical gas sensor comprises at least one polychromatic light source and at least n spectral filters each being configured to detect one of the n different gases,
   the coefficients of the absorptivity matrix ε correspond or are uniformly proportional to mean spectral absorption coefficients of each of then different gases, weighted or not by spectral responses of the n spectral filters, and
   the values of the n detection wavelengths determined in step b) correspond to wavelengths at which the spectral responses of the n spectral filters are located.

4. The method according to claim 3, wherein the coefficients of the absorptivity matrix ε are $\bar{\varepsilon}_j(\lambda_i)$, where:

$$\bar{\varepsilon}_j(\lambda_i) = \frac{\int \varepsilon_j(\lambda) A_i(\lambda) S(\lambda) d\lambda}{\int A_i(\lambda) S(\lambda) d\lambda}$$

or $$\bar{\varepsilon}_j(\lambda_i) = \int \varepsilon_j(\lambda) A_i(\lambda) S(\lambda) d\lambda$$

where $\lambda_i$ corresponds to the n detection wavelengths, with $1 \leq i \leq n$,
$\varepsilon_j(\lambda)$ corresponds to the spectral absorption coefficients for the n different gases, with $1 \leq j \leq n$,
$A_i(\lambda)$ corresponds to the spectral responses of the n spectral filters, and
$S(\lambda)$ corresponds to the emission spectrum of the at least one polychromatic light source.

5. The method according to claim 4, wherein:
the n spectral filters are chosen from amongst a set of m spectral filters, where m>n, of which an outline profile, a wavelength value at which a spectral response is located and a width of the spectral response of each of the m spectral filters of said set of m spectral filters are predetermined, and
the values of the n detection wavelengths are chosen from values of wavelengths at which the spectral responses of the m spectral filters of the said set of m spectral filters are positioned.

6. The method according to claim 3, wherein:
the n spectral filters have a same outline profile, $A(\lambda)$, and the coefficients of the absorptivity matrix ε are $\bar{\varepsilon}_j(\lambda_i)$, where:

$$\bar{\varepsilon}_j(\lambda_i) = \frac{\int A_i(\lambda) \varepsilon_j(\lambda) S(\lambda) d\lambda}{\int A_i(\lambda) S(\lambda) d\lambda}$$

or $$\bar{\varepsilon}_j(\lambda_i) = \int \varepsilon_j(\lambda) A_i(\lambda) S(\lambda) d\lambda$$

where $\lambda_i$ corresponds to the n detection wavelengths, with $1 \leq i \leq n$,
$\varepsilon_j(\lambda)$ corresponds to the spectral absorption coefficients for the n different gases, with $1 \leq j \leq n$,
$A_i(\lambda)$ corresponds to the spectral responses of the n spectral filters positioned at the n detection wavelengths $\lambda_i$, and
$S(\lambda)$ corresponds to the emission spectrum of the at least one polychromatic light source.

7. The method according to claim 6, wherein:
spectral response widths of the n spectral filters are adjustable,
the calculating of step a) is repeated several times, each time by modifying a width of the spectral responses of the n spectral filters, and
the determining of step b) determines the values of the n detection wavelengths for which the value of the determinant of the absorptivity matrix ε corresponds to a maximum calculated value amongst a set of values calculated during the repeated calculating of step a).

8. The method according to claim 1, wherein the steps a) and b) are implemented via an optimisation method of the evolutionary algorithm equation solver type.

9. The method according to claim 1, wherein:
the optical gas sensor comprises n spectral filters each being configured to detect one of the n different gases and one reference filter, and
the method includes determining coefficients of the absorptivity matrix based upon a difference between absorptivity of one of the gases on a path through a corresponding filter and absorptivity of the one gas on a path through the reference filter.

10. A method for optimising values of n detection wavelengths of an optical gas sensor configured to detect n different gases, the method comprising:
   a) calculating a value of a determinant of an absorptivity matrix ε whose coefficients represent spectral absorptivity of each of the n different gases at the n detection wavelengths, said calculating being repeated several times, each time modifying at least one of said n detection wavelengths so the values of said n detection wavelengths are comprised within a range of values for which the spectral absorptivity of at least one of then different gases is non-zero; and
   b) determining the values of said n detection wavelengths for which the calculated value of the determinant of the absorptivity matrix ε corresponds to a maximum calculated value amongst a set of values calculated in step a),
wherein:
   the optical gas sensor does not comprise a reference path and comprises n+1 measurement paths, and
   the coefficients of the absorptivity matrix ε correspond or are uniformly proportional to spectral absorption coefficients, mean or not, of each of the n different gases, weighted or not by spectral responses of the n spectral filters, from which are subtracted spectral absorption coefficients of one of the n+1 measurement paths of the optical gas sensor serving as a reference path.

11. A method for configuring at least n laser light sources of an optical gas sensor detecting n different gases, comprising:
   a) calculation of a value of a determinant of an absorptivity matrix ε whose coefficients represent the spectral absorptivity of each of the n gases at n detection wavelengths, step a) being repeated several times, each time modifying at least one of said n detection wavelengths and such that the values of said n detection wavelengths are comprised within a range of values for which the spectral absorptivity of at least one of the n gases is non-zero;
   b) determination of the values of said n detection wavelengths for which the value of the determinant of the absorptivity matrix c corresponds to the maximum value amongst the set of values calculated in step a); and
   c) tuning of then laser light sources such that the wavelengths of light beams emitted by the n laser light sources correspond to the values of the n detection wavelengths determined in step b).

12. A method for configuring at least n spectral filters of an optical gas sensor detecting n different gases, comprising:
   a) calculation of a value of a determinant of an absorptivity matrix s whose coefficients represent the spectral absorptivity of each of the n gases at n detection wavelengths, step a) being repeated several times, each time modifying at least one of said n detection wavelengths and such that the values of said n detection wavelengths are comprised within a range of values for which the spectral absorptivity of at least one of the n gases is non-zero;
   b) determination of the values of said n detection wavelengths for which the value of the determinant of the absorptivity matrix c corresponds to the maximum value amongst the set of values calculated in step a); and
   c) tuning of the n spectral filters such that the wavelengths at which the spectral responses of the n spectral filters are located correspond to the values of the n detection wavelengths determined in step b).

* * * * *